United States Patent
Hegazi et al.

(10) Patent No.: US 10,371,633 B2
(45) Date of Patent: Aug. 6, 2019

(54) DETERMINING A SPECIFIC GRAVITY OF A SAMPLE

(71) Applicant: Saudi Arabian Oil Company, Dhahran (SA)

(72) Inventors: Ezzat Hegazi, Ontario (CA); Vincent Cunningham, Ferbane (IE); Maha Ali N. Alsayegh, Alkhobar (SA)

(73) Assignee: Saudi Arabian Oil Company, Dhahran (SA)

( * ) Notice: Subject to any disclaimer, the term of this patent is extended or adjusted under 35 U.S.C. 154(b) by 87 days.

(21) Appl. No.: 15/797,938

(22) Filed: Oct. 30, 2017

(65) Prior Publication Data

US 2019/0128809 A1     May 2, 2019

(51) Int. Cl.
    *G01N 21/64*      (2006.01)
    *G01N 33/24*      (2006.01)

(52) U.S. Cl.
    CPC ........... *G01N 21/64* (2013.01); *G01N 33/241* (2013.01)

(58) Field of Classification Search
    CPC .............................. G01N 21/64; G01N 33/241
    See application file for complete search history.

(56) References Cited

U.S. PATENT DOCUMENTS

| | | | |
|---|---|---|---|
| 4,814,614 A * | 3/1989 | Tsui | E21B 49/005 250/255 |
| 5,049,738 A | 9/1991 | Gergely et al. | |
| 5,780,850 A * | 7/1998 | DeLaune | E21B 49/005 250/255 |
| 6,633,043 B2 * | 10/2003 | Hegazi | G01N 21/6408 250/458.1 |
| 7,084,392 B2 * | 8/2006 | DiFoggio | E21B 49/08 250/269.1 |
| 7,202,947 B2 | 4/2007 | Nirmala et al. | |

(Continued)

FOREIGN PATENT DOCUMENTS

| | | |
|---|---|---|
| AU | 2007309735 | 5/2008 |
| CA | 2758971 | 10/2010 |

(Continued)

OTHER PUBLICATIONS

Mishra, "A fluorimetric device for in situ estimation of adulteration in liquid petroleum products", Patent (Indian), No. 200561, Awarded on May 24, 2005, 6 pages.

(Continued)

*Primary Examiner* — David P Porta
*Assistant Examiner* — Djura Malevic
(74) *Attorney, Agent, or Firm* — Fish & Richardson P.C.

(57) ABSTRACT

Methods and systems use fluorescence to determine specific gravity of samples. A first light pulse is applied to a sample at a first angle-of-incidence. A second light pulse is applied to the sample at a second angle-of-incidence. A first ratio based on the intensity of a first fluorescence emission over a first time interval and the intensity of the first fluorescence emission over a second time interval is calculated. A second ratio based on the intensity of a second fluorescence emission over a third time interval and the intensity of the second fluorescence emission over a fourth time interval is calculated. An intensity ratio based on the first ratio and the second ratio is calculated. A specific gravity of the sample based on the intensity ratio is determined.

20 Claims, 7 Drawing Sheets

(56) References Cited

U.S. PATENT DOCUMENTS

| | | | |
|---|---|---|---|
| 8,455,845 B2 | 6/2013 | Hegazi et al. | |
| 8,980,179 B2 | 3/2015 | Geddes | |
| 9,081,175 B2 | 7/2015 | Yang | |
| 9,222,929 B2 | 12/2015 | Chakrabarty et al. | |
| 9,284,227 B2 | 3/2016 | Niccolls et al. | |
| 9,429,556 B2 | 8/2016 | Koseoglu | |
| 2003/0141459 A1* | 7/2003 | Hegazi | G01N 21/6408 250/461.1 |
| 2004/0104355 A1* | 6/2004 | DiFoggio | E21B 49/08 250/461.1 |
| 2004/0218176 A1* | 11/2004 | Shammai | E21B 49/081 356/326 |
| 2010/0044673 A1* | 2/2010 | Tsukada | B82Y 30/00 257/13 |
| 2014/0190254 A1* | 7/2014 | Bouyer | G01V 7/14 73/382 G |
| 2014/0208826 A1 | 7/2014 | Larter et al. | |
| 2014/0291551 A1 | 10/2014 | Rengifo et al. | |
| 2014/0367098 A1 | 12/2014 | Likhanova et al. | |
| 2016/0084815 A1 | 3/2016 | Cuero Rengifo et al. | |
| 2016/0108687 A1 | 4/2016 | Rapoport | |
| 2016/0238526 A1 | 8/2016 | Fadaei et al. | |
| 2016/0363533 A1 | 12/2016 | Koseoglu et al. | |

FOREIGN PATENT DOCUMENTS

| | | |
|---|---|---|
| CA | 2722497 | 6/2011 |
| CA | 2844832 | 2/2013 |
| CA | 2916490 | 2/2013 |
| CA | 2899348 | 10/2015 |
| CA | 2909029 | 12/2015 |
| CA | 2940007 | 10/2016 |
| CA | 2952035 | 2/2017 |
| CA | 2952398 | 2/2017 |
| CN | 102448720 | 5/2012 |
| CN | 104837953 | 8/2015 |
| EP | 2320026 | 5/2011 |
| EP | 2419271 | 2/2012 |
| GB | 2454071 | 4/2009 |
| IN | 200404108 P1 | 4/2009 |
| JP | H05-960052 B2 | 3/1993 |
| KR | 2012007052 A | 1/2012 |
| WO | WO2005017316 A1 | 2/2005 |
| WO | 2008051299 | 5/2008 |
| WO | WO2010010751 A1 | 1/2010 |
| WO | 2010121143 | 10/2010 |
| WO | 2011071651 | 6/2011 |
| WO | 2013023299 | 2/2013 |
| WO | 2013074761 | 5/2013 |
| WO | 2014190000 | 11/2014 |
| WO | 2016111997 | 7/2016 |
| WO | WO2016201254 A1 | 12/2016 |

OTHER PUBLICATIONS

Nandakumar et al., "Method of Detecting API Gravity of Oil Present in Hydrocarbon Bearing Fluid Inclusions," Indian Patent Application No. 1559/CHE/2015, Filed Mar. 26, 2015, 24 pages.

International Search Report and Written Opinion issued in International Application No. PCT/US2018/056982 dated Jan. 3, 2019, 15 pages.

Patra and Mishra, "Effect of sample geometry on synchronous fuorimetric analysis of petrol, diesel, kerosene and their mixtures at higher concentration," Analyst, vol. 125 (2000), pp. 1383-1386.

* cited by examiner

DETERMINING A SPECIFIC GRAVITY OF A SAMPLE

TECHNICAL FIELD

This disclosure relates to fluid fluorescence.

BACKGROUND

Some fluids can fluoresce, that is, they give off light when stimulated by a certain wavelength of light from an external source. Different fluids are sensitive to different wavelengths of light and different fluids fluoresce different wavelengths of light when stimulated or excited.

SUMMARY

This disclosure describes methods and systems for characterizing fluids based on fluorescence of the fluids. These method and systems allow technicians to quickly characterize fluids in the field at remote work sites based on their API gravity, avoiding the time and difficulty of sending samples to an off-site laboratory for analysis.

In one aspect, methods include: applying a first light pulse to a sample at a first angle-of-incidence; detecting an intensity of a first fluorescence emission emitted from the sample over a first time interval and a second time interval; applying a second light pulse to the sample at a second angle-of-incidence; detecting an intensity of a second fluorescence emission emitted from the sample over a third time interval and a fourth time interval; calculating, by a processor, a first ratio based on the intensity of the first fluorescence emission over the first time interval and the intensity of the first fluorescence emission over the second time interval; calculating, by a processor, a second ratio based on the intensity of the second fluorescence emission over the third time interval and the intensity of the second fluorescence emission over the fourth time interval; calculating, by a processor, an intensity ratio based on the first ratio and the second ratio; and determining a specific gravity of the sample based on the intensity ratio.

In one aspect, methods include: applying a first light pulse to a sample at a first angle-of-incidence; detecting an intensity of a first fluorescence emission as the intensity of the first fluorescence emission fades; applying a second light pulse to the sample at a second angle-of-incidence; detecting an intensity of a second fluorescence emission as the intensity of the second fluorescence emission fades; comparing, by a processor, the fading of the first fluorescence emission with the fading of the second fluorescence emission; and determining a specific gravity of the sample based on a ratio calculated based on a comparison of the fading of the first fluorescence emission and the fading of the second fluorescence emission.

In one aspect, an API gravity measurement system includes: a fluorescence-measuring apparatus, including: a first single-wavelength light source configured to generate a first excitation light pulse to contact a sample at a first angle-of-incidence; a second single-wavelength light source configured to generate a second excitation light pulse to contact the sample at a second-angle of incidence; a sample holder configured to hold the sample; and a detector configured to detect an intensity of a fluorescence emission from the sample; a processor; and a computer-readable storage medium storing instructions executable by the processor, the instructions including: applying a first light pulse to a sample at a first angle-of-incidence; detecting an intensity of a first fluorescence emission emitted from the sample over a first time interval and a second time interval; applying a second light pulse to the sample at a second angle-of-incidence; detecting an intensity of a second fluorescence emission emitted from the surface over a third time interval and a fourth time interval; calculating, by a processor, a first ratio based on the intensity of the first fluorescence emission over the first time interval and the intensity of the first fluorescence emission over the second time interval; calculating, by a processor, a second ratio based on the intensity of the second fluorescence emission over the third time interval and the intensity of the second fluorescence emission over the fourth time interval; calculating, by a processor, an intensity ratio based on the first ratio and the second ratio; and determining a specific gravity of the sample based on the intensity ratio.

Embodiments of these methods and systems can include one or more of the following features.

Some embodiments include applying the first light pulse includes producing the first light pulse using a first single-wavelength light source. In some cases, the first single-wavelength light source includes a laser operating at 250 to 450 nanometers (nm). In some cases, applying the second light pulse includes producing the second light pulse using the first single-wavelength light source. Methods can include moving the first single-wavelength light source between producing the first light pulse and producing the second light pulse, moving the sample between producing the first light pulse and producing the second light pulse, or both.

In some embodiments, applying the second light pulse includes producing the second light pulse using a second single-wavelength light source.

In some embodiments, the sample includes hydrocarbon fluid and the specific gravity is an API gravity.

In some embodiments, the first angle-of-incidence is between 5 and 30 degrees.

In some embodiments, the second angle-of-incidence is between 40 and 65 degrees.

In some embodiments, the difference between the first angle-of-incidence and the second angle-of-incidence is between 25 and 65 degrees.

In some embodiments, methods and systems also include: normalizing, by a processor, the first fluorescence emission over the first time interval and the second time interval; and normalizing, by a processor, the second fluorescence emission over the third time interval and the fourth time interval.

In some embodiments, the first time interval and the third time interval are synchronized to a maximum of the first light pulse and the second light pulse, respectively.

In some embodiments, the second time interval and the fourth time interval are synchronized to 3 nanoseconds (ns) after a maximum of the first light pulse and the second light pulse, respectively.

BRIEF DESCRIPTION OF DRAWINGS

Like reference numbers and designations in the various drawings indicate like elements.

DETAILED DESCRIPTION

This disclosure describes methods and systems for characterizing fluids based on fluorescence of the fluids. These method and systems allow technicians to quickly characterize fluids in the field at remote work sites based on their API gravity, avoiding the time and difficulty of sending samples to an off-site laboratory for analysis.

Figure 1:
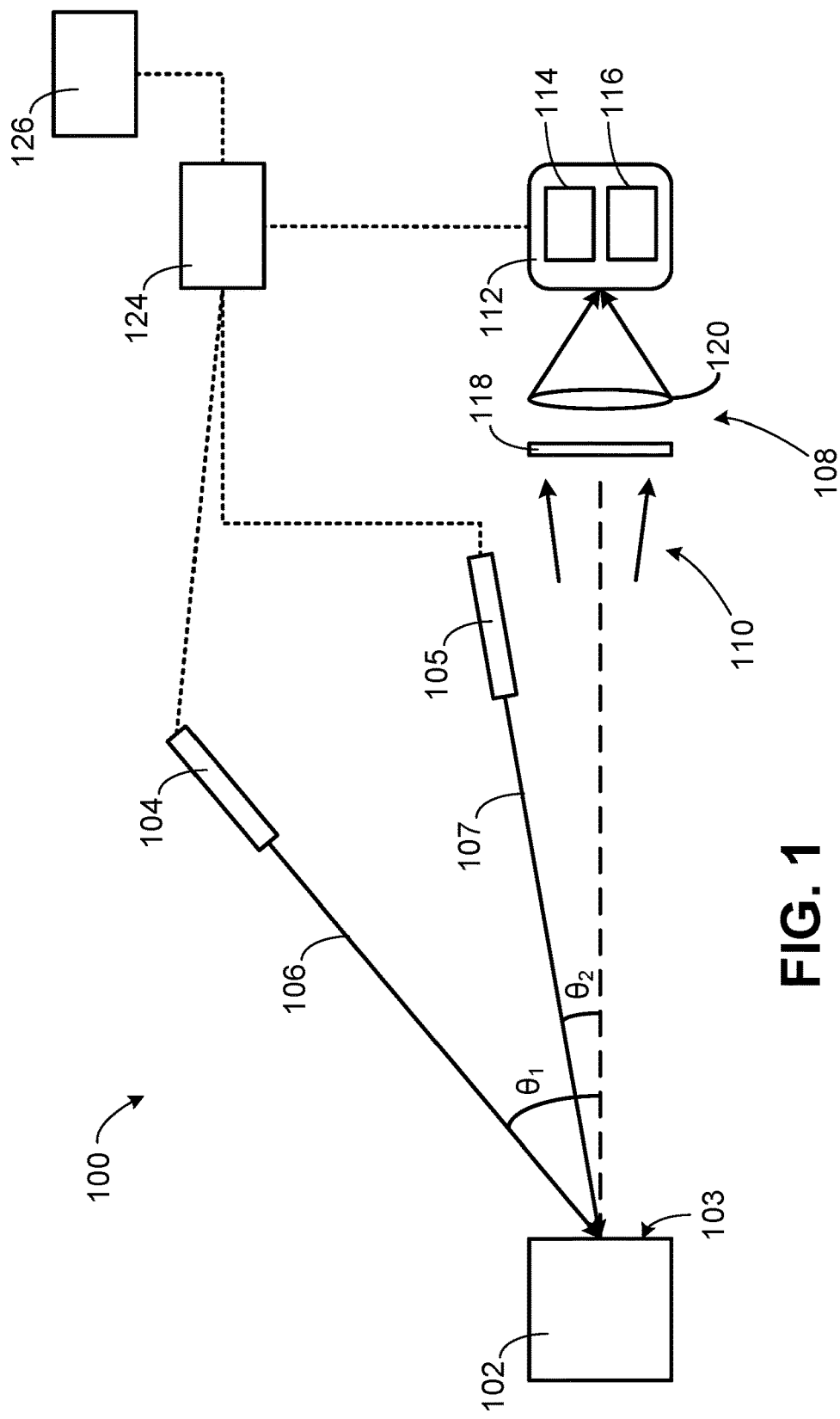
FIG. 1 is a schematic diagram of an example fluorescence-measurement apparatus.

FIG. 1 shows an API gravity measurement apparatus 100. The API gravity measurement apparatus 100 is configured to measure variations in fluorescent intensities based on incident angles of an excitation light. At a high level, the apparatus 100 includes a sample holder 102, a first excitation light source 104 configured to direct excitation light on the sample holder 102 at a first angle-of-incidence $\theta_1$ relative to a normal surface 103 of the sample holder 102, and a detector 112 configured to detect fluorescence intensity in response to the excitation light. For example, the 0 degree angle represented with the dashed line is perpendicular to a surface of a cuvette holding the sample. The apparatus 100 also includes a second excitation light source 105 configured to direct excitation light on the sample holder 102 at a second angle-of-incidence $\theta_2$ relative to a normal surface 103 of the sample holder 102. By plotting and analyzing the fluorescence intensity spectra captured at different times after excitation at each angle-of-incidence, the apparatus 100 determines the API gravity of a sample contained in the sample holder 102.

The sample holder 102 defines an inner cavity capable of holding a sample, such as a fluid. The surface 103 of the sample holder 102 is transparent to an excitation light source 104. In some implementations, the sample holder 102 is a quartz cuvette, a glass sample container, or any other sample container with a flat surface that is transparent to the specified wavelengths of the light source 104. In some implementations, only a single side of the sample holder is transparent to the specified wavelengths of the light source 104.

The excitation light sources 104 and 105 emit beams 106 and 107, respectively, of a single wavelength of light that is capable of generating fluorescence in a sample. In some implementations, the excitation light source 104 emits a beam 106 of light containing multiple wavelengths with at least one wavelength that is capable of generating fluorescence in the sample. In some implementations, the light sources 104 and 105 are lasers that emit laser beams at a defined wavelength, for example, an ultraviolet wavelength. In some implementations, the wavelength of the light beams 106 and 107 is between 250 nanometers and 450 nanometers.

Some systems also include one or more optical components positioned between the sample holder 102 and the detector 112. The apparatus 100 includes optical components 108 positioned in a path of fluorescence emission 110 from the surface of the sample holder 102. The optical components 108 of apparatus 100 include a filter 118 positioned between the surface of the sample holder 102 and the detector 112 and a lens 120 positioned between the filter 118 and the detector 112. The filter 118 passes a specified range of wavelengths and filters out or otherwise blocks wavelengths outside the specified range. The filter 118 can be a notch filter or any other optical filter. The lens 120 is configured to focus the fluorescence emission 110. In some implementations, the optical components include different or less components than the illustrated optical components 108 without departing from the scope of the disclosure. For example, in some implementations, the lens focuses the fluorescence emission on an inlet of a fiber optic cable. The fiber optic cable can be configured to guide or otherwise pass the focused light from the inlet to an outlet. In some implementations, the lens 120 focuses the light directly onto the detector 112 without including a fiber optic cable. The lens can include a quartz convex lens, or any other lens appropriate for the wavelengths being measured.

The detector 112 detects an intensity of the fluorescence emission 110. Examples of detected intensities are described later within this disclosure. The detector 112 of apparatus 100 includes a monochromator 114 coupled to a photomultiplier 116. The monochromator 114 spatially disperses the fluorescence emission 110 into spectral components while the photomultiplier acts to amplify the detected fluorescence emission 110.

The apparatus 100 also includes a microprocessor 124 and a computer-readable storage medium 126 that stores instructions executable by the microprocessor 124. Details on such processes are described later within the specification.

In some aspects of operation, after an excitation light beam 106 or 107 impacts the sample 102, a reflected light is directed to a beam dump (not shown) while the fluorescent light 110 is emitted towards the detector 112.

All of the previously described components can be combined into a compact, portable unit that can be used in field operations.

In some implementations, rather than having a first excitation light source 104 and a second excitation light source 105, the apparatus includes a single excitation light source that is moveable such that it may produce a beam to contact the sample holder 102 at a range of angles-of-incidence.

Figure 2:
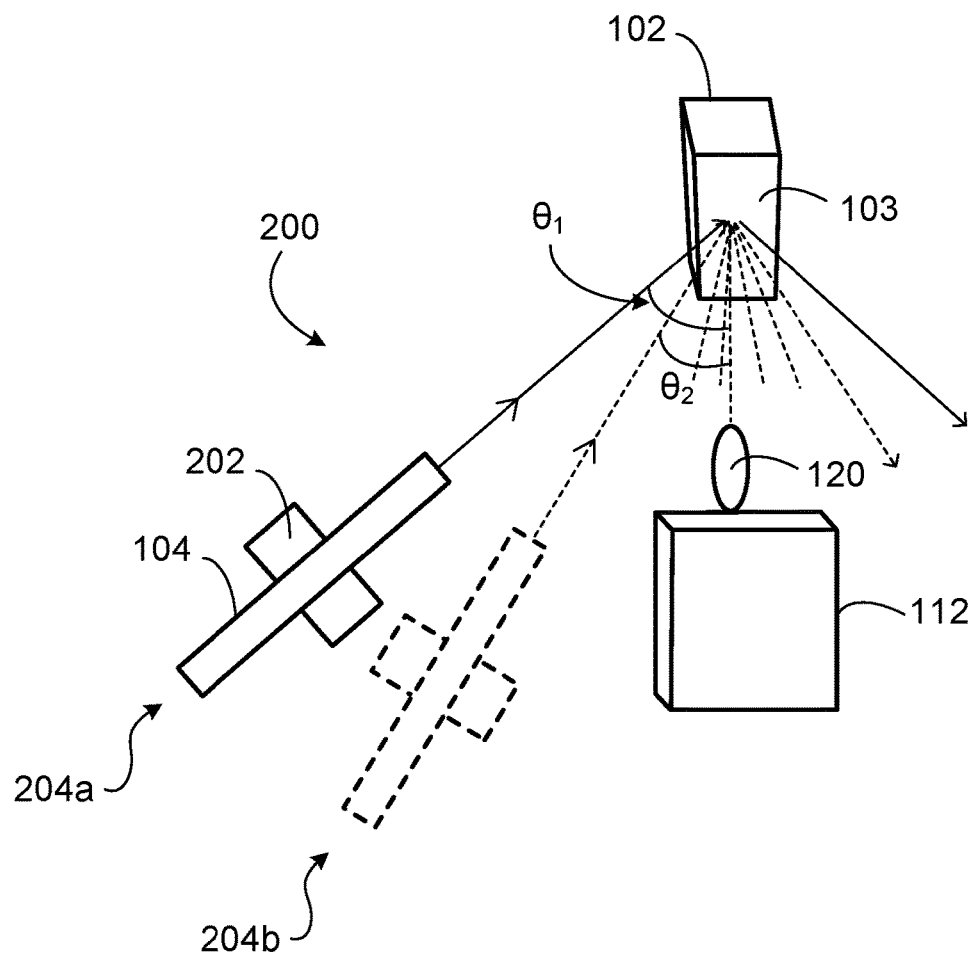
FIG. 2 is a schematic diagram showing light sources for the fluorescence-measurement apparatus.

FIG. 2 shows an apparatus 200 in which the light source 104 moves in order to adjust the angle of incidence. Apparatus 200 includes a movable mount 202 is attached to the light source 104. The movable mount 202 changes an incident angle of the excitation light source 104 relative to the surface 103 of the sample holder 102 as the moveable mount 202 moves from a first position 204a to a second position 204b. The mount 202 moves the single excitation light source 104 in an arc around the sample holder 102. The angles-of-incidence that are achieved between the normal surface 103 and the light source 104 range from 5 to approximately 75 degrees. In some implementations, a beam catcher moves in conjunction with the light source 104 or the sample holder 102 to capture reflected light.

The apparatuses 100 and 200 are used to capture fluorescence emission spectra of the sample.

FIGS. 3A-3D are plots of normalized emission spectra plotted based upon an intensity of the fluorescent emissions 110 (see FIG. 1) emitted from a sample within the sample holder 102 (see FIG. 1). A laser source operating at 266 nm was used to excite samples from two different laser angles-of-incidence (10 degrees and 40 degrees). For each of the angles-of-incidence, the fluorescence emission was measured over five consecutive time periods. The first time period was synchronized to the maximum of the laser beam pulse from the excitation light source. The second time period was 3 ns after the maximum, the third was 6 ns after the maximum, the fourth was 9 ns after the maximum, and the fifth was 12 ns after the maximum. The gate width for each time period was selected to be 3 ns. These figures presents the spectra 300 for an angle of incidence of 10 degrees separately from the spectra 300 for an angle of incidence of 40 degrees. In these plots, spectra 302 represents fluorescent emissions captured in the first time period (TG1) and spectra 304 represents fluorescence emissions captured in the second time period (TG2).

The spectra are normalized, meaning that the spectra representing fluorescence emissions captured in the second through the fifth time periods are plotted relative to the spectra representing fluorescence emissions captured in the first time period.

For each of the two angles-of-incidence at which the sample was excited, an intensity ratio was calculated by dividing a value of relative intensity 308 of the spectra 304 at a wavelength by a value of relative intensity 306 of the spectra 302 at the same wavelength to calculate an intensity ratio. After calculating an intensity ratio between the TG1 spectrum and the TG2 spectrum for each angle-of-incidence, a final intensity ratio was calculated by dividing the intensity ratio at the smaller angle-of-incidence by the intensity ratio at the larger angle-of-incidence.

The vertical lines mark the location of the optically filtered 420 nm intensity wavelength. Comparison of the spectra 300 for an angle of incidence of 10 degrees with the spectra 301 for an angle of incidence of 40 degrees demonstrates that the intensity ratio at 420 nm between TG1 spectra 302 and TG2 spectra 304 is dependent on the angle-of-incidence of the excitation beam. It can also be observed that this phenomenon is not only present at the 420 nm, but for all wavelengths throughout the spectrum. As such, in some implementations, the intensity ratios may be calculated for any wavelength throughout the spectrum. The 420 nm wavelength was chosen because corresponds to the region of maximum fluorescence intensity for crude oils when excited by ultraviolet light. As can be seen in FIGS. 3A-3D, this wavelength is near but not necessarily at the maximum intensity for the observed spectra.

Figure 3A:
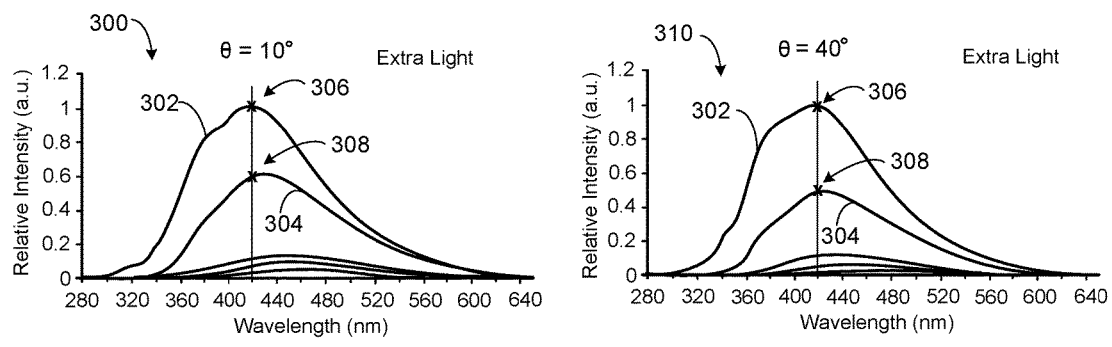
FIGS. 3A-3D are example plots of fluorescent intensities for different potential samples with light sources positioned at different angles.

FIG. 3A presents the results for an extra light crude oil sample with an API gravity of 39.2 as determined using traditional API gravity measurement techniques. Using the previously described approach, the intensity ratio for this sample was approximately 0.6 for the 10-degree spectra 300 and approximately 0.45 for 40-degree spectra 300. The final intensity ratio for this sample was approximately 1.33.

Figure 3B:
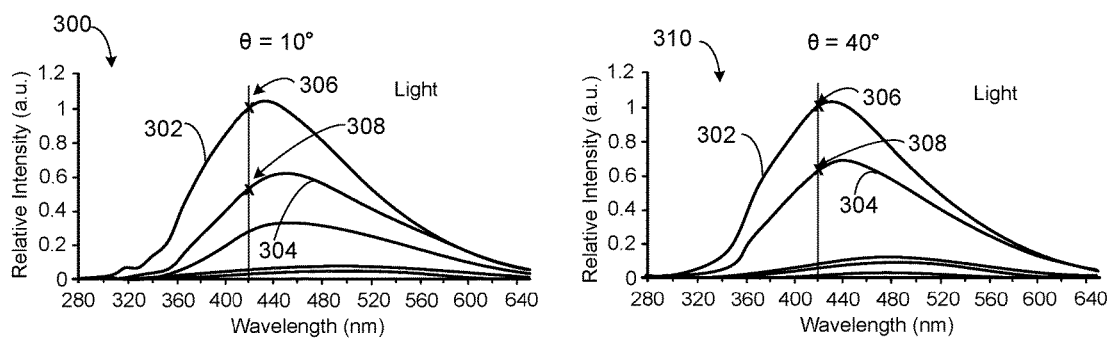

FIG. 3B presents the results for a light crude oil sample with an API gravity of 34.1 as determined using traditional API gravity measurement techniques. Using the previously described approach, the intensity ratio for this sample was approximately 0.54 for the 10-degree spectra 300 and approximately 0.63 for 40-degree spectra 300. The final intensity ratio for this sample was approximately 0.86.

Figure 3C:
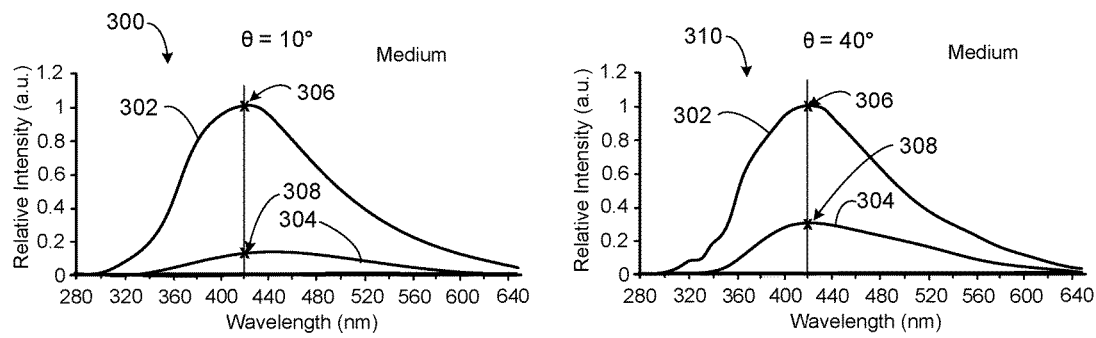

FIG. 3C presents the results for a medium crude oil sample with an API gravity of 30.2 as determined using traditional API gravity measurement techniques. Using the previously described approach, the intensity ratio for this sample was approximately 0.14 for the 10-degree spectra 300 and approximately 0.32 for 40-degree spectra 300. The final intensity ratio for this sample was approximately 0.43.

Figure 3D:
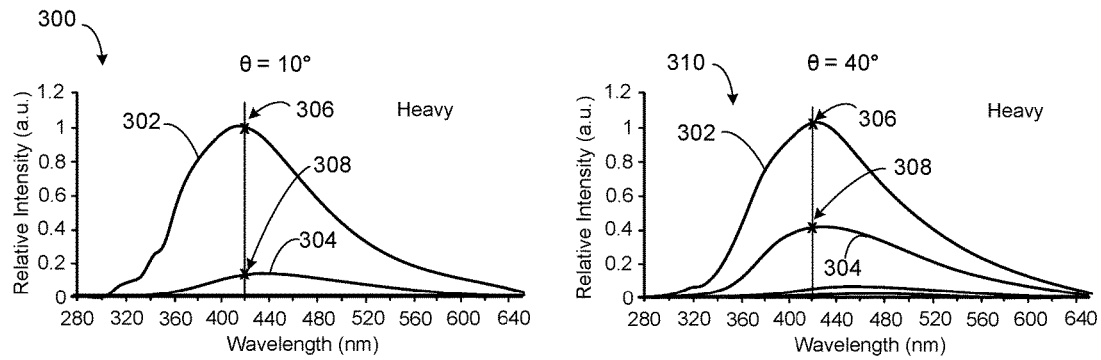

FIG. 3D presents the results for a heavy crude oil sample with an API gravity of 27.4 as determined using traditional API gravity measurement techniques. Using the previously described approach, the intensity ratio for this sample was approximately 0.32 for the 10-degree spectra 300 and approximately 0.43 for 40-degree spectra 300. The final intensity ratio for this sample was approximately 0.32.

Figure 4:
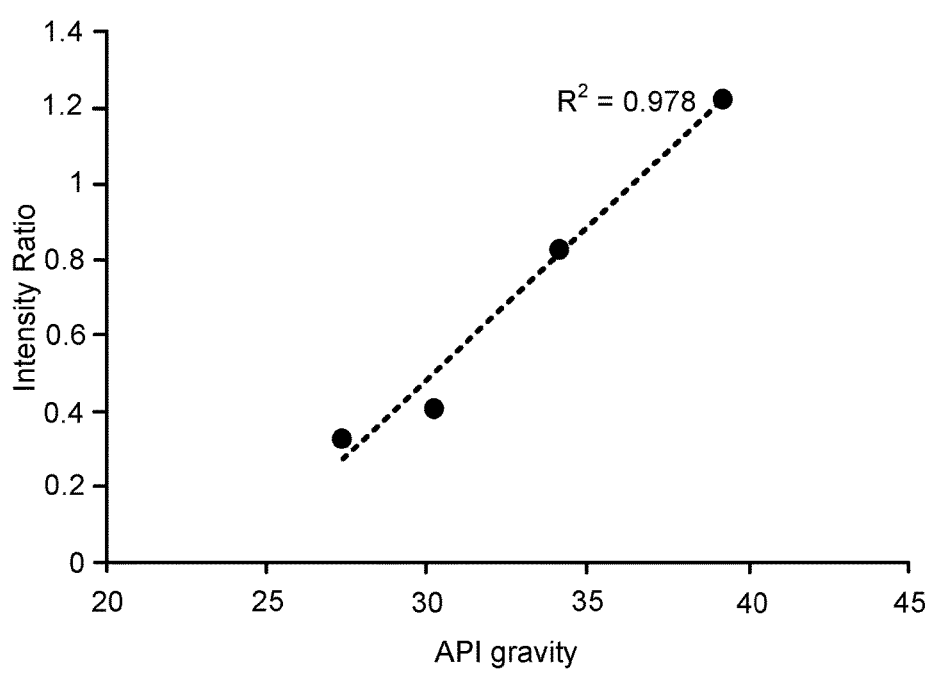
FIG. 4 is an example plot of fluorescent intensity ratios versus American Petroleum Institute (API) gravity.

FIG. 4 plots final intensity ratios versus API gravity for the samples discussed with respect to FIGS. 3A-3D. A regression analysis was performed and indicated that $$\text{API gravity} = (\text{final intensity ratio} + 1.961)/0.082$$

describes the relationship between the final intensity ratio and the API gravity for the API gravity measurement apparatus 100 discussed with respect to FIG. 1. The coefficient of determination ($R^2$) of the regression analysis was, in this example, 0.978, showing a high degree of predictability between the final intensity ratio and the API gravity of a sample.

Differing angles-of-incidence may be selected for emitting the first and second light pulses. The first angle-of-incidence may be between 5 and 30 degrees and the second angle-of-incidence may be between 40 and 65 degrees. A difference between the first and second angles of incidence may be between 25 and 65 degrees. Based upon the angles of incidence selected for emitting the first and second light pulses, the equation for comparing the final intensity ratio to the API gravity may change.

Figure 5:
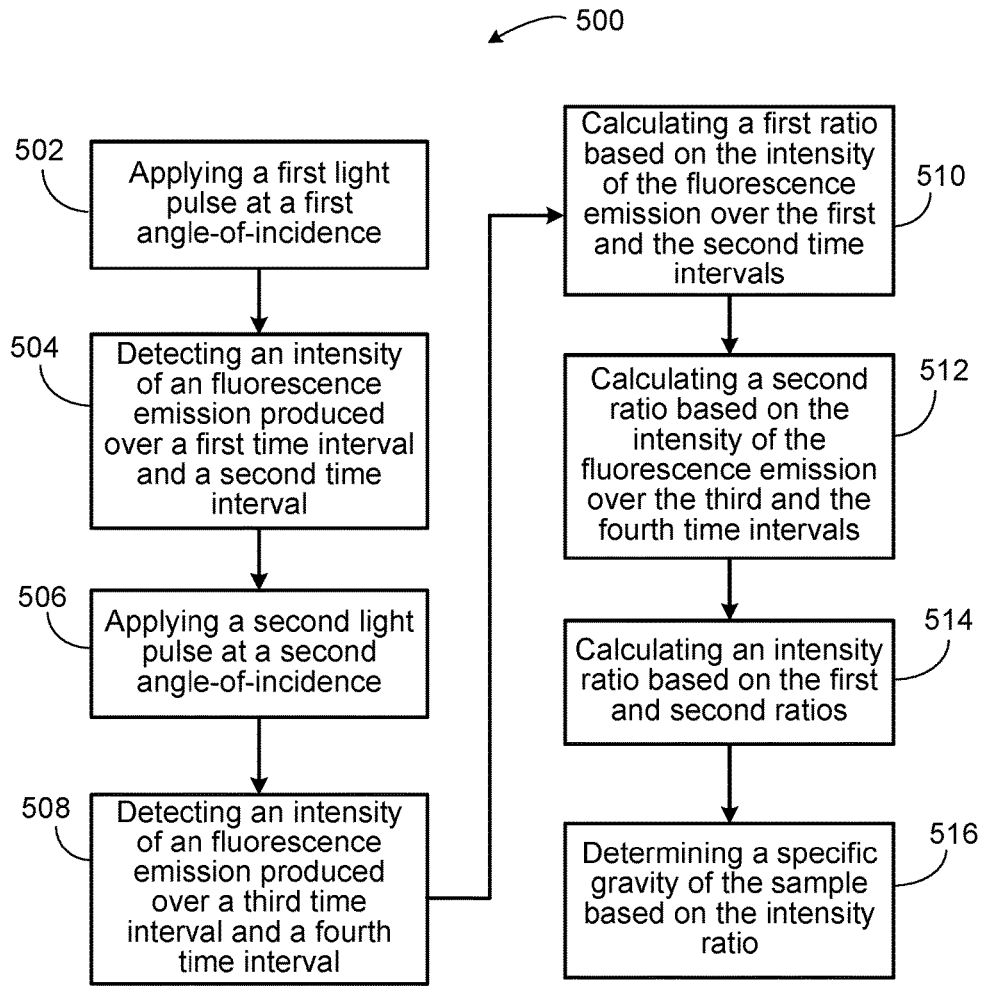
FIG. 5 is a flowchart of an example method for calculating an API gravity of a sample using fluorescent intensities.

FIG. 5 is a flowchart showing an example method 500 that can be used to determine a specific gravity (for example, an API gravity) of a sample. At 502, a first light pulse is applied to the sample at a first angle-of-incidence. The first angle-of-incidence may be between 5 and 30 degrees. At 504, an intensity of a first fluorescence emission emitted from the sample over a first time interval and a second time interval is detected. At 506, a second light pulse to the sample at a second angle-of-incidence is applied to a sample. The second angle-of-incidence may be between 40 and 65 degrees. At 508, an intensity of a second fluorescence emission emitted from the sample over a third time interval and a fourth time interval is detected. At 510, a first ratio based on the intensity of the first fluorescence emission over the first time interval and the intensity of the first fluorescence emission over the second time interval is calculated by a processor. At 512, a second ratio based on the intensity of the second fluorescence emission over the third time interval and the intensity of the second fluorescence emission over the fourth time interval is calculated by a processor. At 514, an intensity ratio based on the first ratio and the second ratio is calculated by a processor. At 516, a specific gravity of the sample is determined based on the intensity ratio. The specific gravity may be determined via a lookup table or via a calculation where inputting the intensity ratio returns the specific gravity. The specific gravity may be an API gravity and the sample may be a hydrocarbon fluid.

Figure 6:
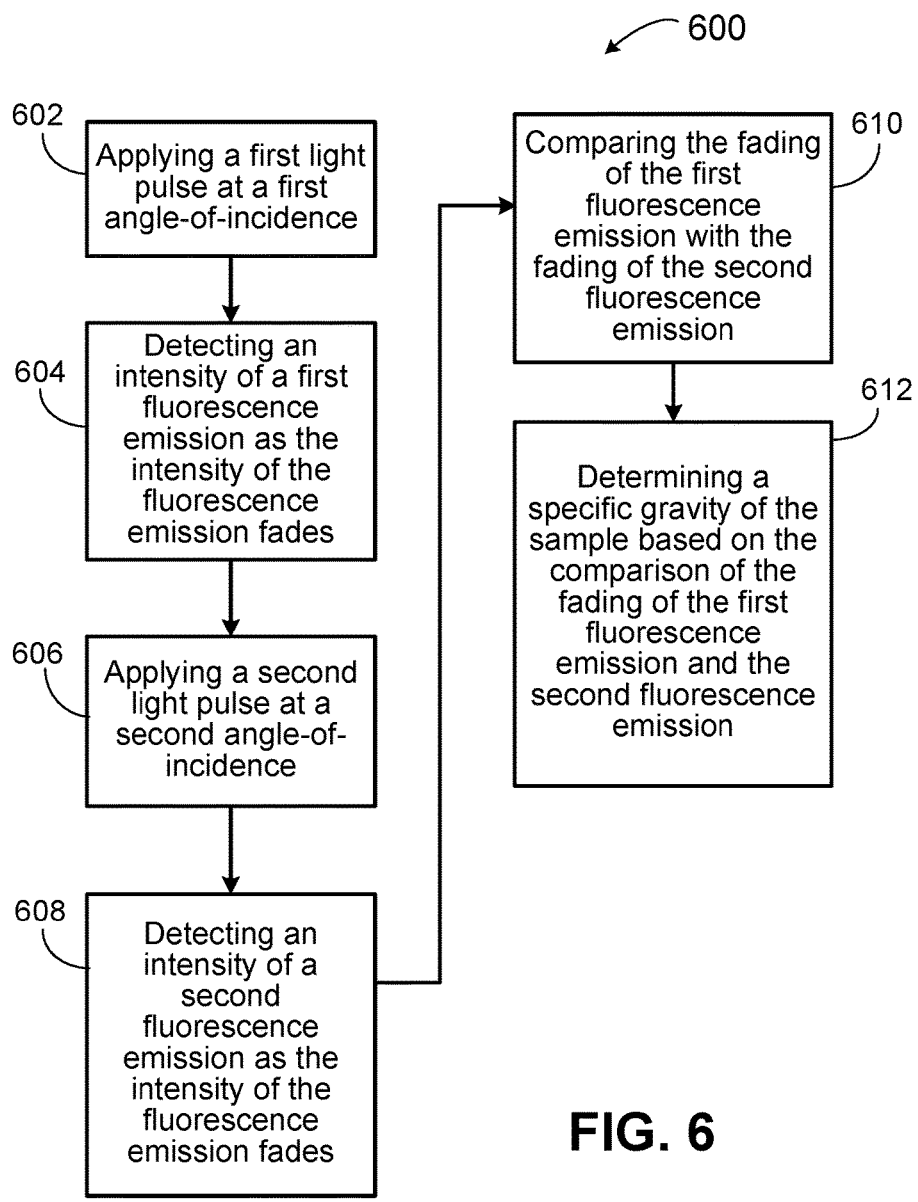
FIG. 6 is a flowchart of an example method for calculating an API gravity of a sample using fluorescent intensities.

FIG. 6 is a flowchart showing another example method 600 that can be used to determine a specific gravity (for example, an API gravity) of a sample. At 602, a first light pulse at a first angle-of-incidence is applied to a sample. The first angle-of-incidence may be between 5 and 30 degrees. At 604, an intensity of a first fluorescence emission is detected as the intensity of the first fluorescence emission fades. An example of a fluorescence emission fading over time is illustrated by the plots of FIGS. 3A-3D which show decreasing fluorescence intensity across the spectrum of wavelengths as time increases (for example, TG1 spectra has higher intensity than TG5 spectra). At 606, a second light pulse at a second angle-of-incidence is applied to the sample. The first angle-of-incidence may be between 5 and 30 degrees. At 608, an intensity of a second fluorescence emission is detected as the intensity of the second fluorescence emission fades. At 610, the fading of the first fluorescence emission with the fading of the second fluorescence emission are compared by a processor. At 612, a specific gravity of the sample is determined based on a ratio calculated based on a comparison of the fading of the first fluorescence emission and the fading of the second fluorescence emission.

Implementations of the subject matter and the operations described in this disclosure can be implemented in digital electronic circuitry, or in computer software, firmware, or hardware, including the structures disclosed in this disclosure and their structural equivalents, or in combinations of one or more of them. Implementations of the subject matter described in this disclosure can be implemented as one or more computer programs, that is, one or more modules of computer program instructions, encoded on computer storage medium for execution by, or to control the operation of, data processing apparatus. Alternatively, or in addition, the program instructions can be encoded on an artificially generated propagated signal, such as, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (such as, multiple CDs, disks, or other storage devices).

The operations described in this disclosure can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, such as, an FPGA (field programmable gate array) or an ASIC (application specific integrated circuit). The apparatus can also include, in addition to hardware, code that creates an execution environment for the computer program in question, such as, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (such as, one or more scripts stored in a markup language document), in a single file dedicated to the program in question, or in multiple coordinated files (such as, files that store one or more modules, sub programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, such as, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, such as, magnetic, magneto optical disks, or optical disks. However, a computer need not have such devices. Moreover, a computer can be embedded in another device, such as, a mobile telephone, a personal digital assistant (PDA), a mobile audio or video player, a game console, a Global Positioning System (GPS) receiver, or a portable storage device (such as, a universal serial bus (USB) flash drive), to name just a few. Devices suitable for storing computer program instructions and data include all forms of non volatile memory, media and memory devices, including by way of example semiconductor memory devices; magnetic disks, such as, internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this disclosure can be implemented on a computer having a display device, such as, a CRT (cathode ray tube) or LCD (fluid crystal display) monitor, for displaying information to the user and a keyboard and a pointing device, such as, a mouse or a trackball, by which the user can provide input to the computer. Other kinds of devices can be used to provide for interaction with a user as well; for example, feedback provided to the user can be any form of sensory feedback, such as, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While this disclosure contains many specific implementation details, these should not be construed as limitations on the scope of what may be claimed, but rather as descriptions of features specific to particular implementations of particular embodiments. Certain features that are described in this disclosure in the context of separate implementations can also be implemented in combination in a single implementation. Conversely, various features that are described in the context of a single implementation can also be implemented in multiple implementations separately or in any suitable sub combination. Moreover, although features may be described as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed to achieve desirable results. Moreover, the separation of various system components in the implementations described should not be understood as requiring such separation in all implementations, and it should be understood that the described components can generally be integrated together in a single product or packaged into multiple products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A method comprising:
    applying a first light pulse to a sample at a first angle-of-incidence;
    detecting an intensity of a first fluorescence emission emitted from the sample over a first time interval and a second time interval;
    applying a second light pulse to the sample at a second angle-of-incidence;
    detecting an intensity of a second fluorescence emission emitted from the sample over a third time interval and a fourth time interval;
    calculating, by a processor, a first ratio based on the intensity of the first fluorescence emission over the first time interval and the intensity of the first fluorescence emission over the second time interval;
    calculating, by a processor, a second ratio based on the intensity of the second fluorescence emission over the third time interval and the intensity of the second fluorescence emission over the fourth time interval;
    calculating, by a processor, an intensity ratio based on the first ratio and the second ratio; and
    determining a specific gravity of the sample based on the intensity ratio.

2. The method of claim 1, wherein applying the first light pulse comprises producing the first light pulse using a first single-wavelength light source.

3. The method of claim 2, wherein the first single-wavelength light source comprises a laser operating at 250 to 450 nm.

4. The method of claim 2, wherein applying the second light pulse comprises producing the second light pulse using the first single-wavelength light source.

5. The method of claim 4, comprising moving the first single-wavelength light source between producing the first light pulse and producing the second light pulse.

6. The method of claim 4, comprising moving the sample between producing the first light pulse and producing the second light pulse.

7. The method of claim 1, wherein applying the second light pulse comprises producing the second light pulse using a second single-wavelength light source.

8. The method of claim 1, wherein the sample comprises hydrocarbon fluid and the specific gravity is an API gravity.

9. The method of claim 1, wherein the first angle-of-incidence is between 5 and 30 degrees.

10. The method of claim 1, wherein the second angle-of-incidence is between 40 and 65 degrees.

11. The method of claim 1, wherein the difference between the first angle-of-incidence and the second angle-of-incidence is between 25 and 65 degrees.

12. The method of claim 1, further comprising:
    normalizing, by a processor, the first fluorescence emission over the first time interval and the second time interval; and
    normalizing, by a processor, the second fluorescence emission over the third time interval and the fourth time interval.

13. The method of claim 1, wherein the first time interval and the third time interval are synchronized to a maximum of the first light pulse and the second light pulse, respectively.

14. The method according to claim 1, wherein the second time interval and the fourth time interval are synchronized to 3 ns after a maximum of the first light pulse and the second light pulse, respectively.

15. A method comprising:
    applying a first light pulse to a sample at a first angle-of-incidence;
    detecting an intensity of a first fluorescence emission as the intensity of the first fluorescence emission fades;
    applying a second light pulse to the sample at a second angle-of-incidence;
    detecting an intensity of a second fluorescence emission as the intensity of the second fluorescence emission fades;
    comparing, by a processor, the fading of the first fluorescence emission with the fading of the second fluorescence emission; and
    determining a specific gravity of the sample based on a ratio calculated based on a comparison of the fading of the first fluorescence emission and the fading of the second fluorescence emission.

16. The method of claim 15, wherein applying the first light pulse comprises producing the first light pulse using a first single-wavelength light source.

17. The method of claim 16, wherein applying the second light pulse comprises producing the second light pulse using the first single-wavelength light source.

18. The method of claim 17, comprising moving the first single-wavelength light source between producing the first light pulse and producing the second light pulse.

19. The method of claim 17, comprising moving the sample between producing the first light pulse and producing the second light pulse.

20. An API gravity measurement system comprising:
    a fluorescence-measuring apparatus, comprising:
    a first single-wavelength light source configured to generate a first excitation light pulse to contact a sample at a first angle-of-incidence;
    a second single-wavelength light source configured to generate a second excitation light pulse to contact the sample at a second-angle of incidence;
    a sample holder configured to hold the sample; and
    a detector configured to detect an intensity of a fluorescence emission from the sample;
    a processor; and a computer-readable storage medium storing instructions executable by the processor, the instructions comprising:
  applying a first light pulse to a sample at a first angle-of-incidence;
  detecting an intensity of a first fluorescence emission emitted from the sample over a first time interval and a second time interval;
  applying a second light pulse to the sample at a second angle-of-incidence;
  detecting an intensity of a second fluorescence emission emitted from the surface over a third time interval and a fourth time interval;
  calculating, by a processor, a first ratio based on the intensity of the first fluorescence emission over the first time interval and the intensity of the first fluorescence emission over the second time interval;
  calculating, by a processor, a second ratio based on the intensity of the second fluorescence emission over the third time interval and the intensity of the second fluorescence emission over the fourth time interval;
  calculating, by a processor, an intensity ratio based on the first ratio and the second ratio; and
  determining a specific gravity of the sample based on the intensity ratio.

\* \* \* \* \*